United States Patent
Pavia et al.

(10) Patent No.: US 9,593,057 B2
(45) Date of Patent: Mar. 14, 2017

(54) METHOD AND APPARATUS FOR REDUCING CONDENSATION IN VAPOR-LIQUID ACID GAS SCRUBBERS

(71) Applicant: ExxonMobil Chemical Patents Inc., Baytown, TX (US)

(72) Inventors: Thomas W. Pavia, Houston, TX (US); William A. Butler, Houston, TX (US); John R. Delaney, Houston, TX (US); Richard A. Symes, Edinburgh (GB)

(73) Assignee: ExxonMobil Chemical Patents Inc., Baytown, TX (US)

(*) Notice: Subject to any disclaimer, the term of this patent is extended or adjusted under 35 U.S.C. 154(b) by 286 days.

(21) Appl. No.: 14/517,237

(22) Filed: Oct. 17, 2014

(65) Prior Publication Data
US 2015/0166440 A1 Jun. 18, 2015

Related U.S. Application Data

(60) Provisional application No. 61/917,207, filed on Dec. 17, 2013.

(30) Foreign Application Priority Data

Feb. 2, 2014 (EP) .................................. 14153946

(51) Int. Cl.
*C07C 7/11* (2006.01)
*B01D 53/00* (2006.01)
(Continued)

(52) U.S. Cl.
CPC .............. *C07C 7/11* (2013.01); *B01D 53/002* (2013.01); *B01D 53/145* (2013.01);
(Continued)

(58) Field of Classification Search
None
See application file for complete search history.

(56) References Cited

U.S. PATENT DOCUMENTS

| 3,598,881 A | 8/1971 | Kniel et al. |
| 3,926,591 A | 12/1975 | Wildmoser et al. |

(Continued)

FOREIGN PATENT DOCUMENTS

| WO | 00/44694 | 8/2000 |

OTHER PUBLICATIONS

Robert A. Meyers, Handbook of Petrochemicals Production Processes, 2005, Part 6 Ethylene, section 6.40-6.41.

*Primary Examiner* — In Suk Bullock
*Assistant Examiner* — Alyssa L Cepluch

(57) ABSTRACT

The invention generally relates to a hydrocarbon process for reducing condensation in a vapor-liquid amine or caustic acid gas scrubber. A first mixture is provided, the first mixture being superheated and comprising $C_{2+}$ mono-olefin, acid gases, and diolefin molecules. The first mixture is divided into a first stream and a second stream, the first and second streams having substantially the same composition. The first stream is cooled to produce a gas phase and a liquid phase, the gas phase comprising less $C_{6+}$, the liquid phase containing more $C_{6+}$. The gas phase is separated to create a third stream. The third stream and the second stream are combined to form a second substantially superheated mixture. The second mixture is conducted to an acid gas scrubbing tower. The invention also relates to an apparatus for carrying out this process.

5 Claims, 1 Drawing Sheet

(51) Int. Cl.
*C10G 75/00* (2006.01)
*B01D 53/14* (2006.01)
*C07C 7/00* (2006.01)
*C10G 70/06* (2006.01)

(52) U.S. Cl.
CPC .......... *B01D 53/1462* (2013.01); *C07C 7/005* (2013.01); *C10G 70/06* (2013.01); *C10G 75/00* (2013.01); *B01D 2252/204* (2013.01)

(56) References Cited

U.S. PATENT DOCUMENTS

| | | | |
|---|---|---|---|
| 7,575,669 B2 | 8/2009 | Subramanlyam | |
| 7,772,449 B2 * | 8/2010 | Kurukchi | B01D 53/1406 208/81 |

* cited by examiner

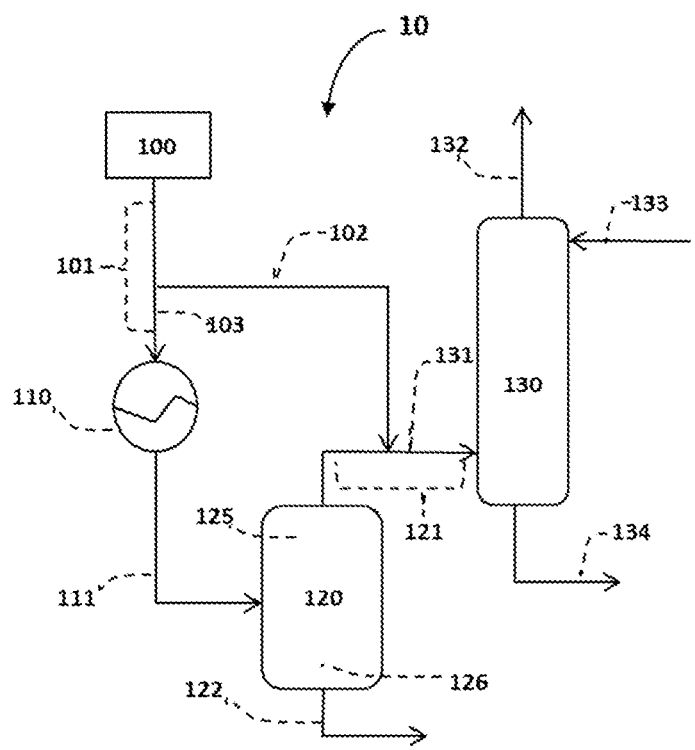

METHOD AND APPARATUS FOR REDUCING CONDENSATION IN VAPOR-LIQUID ACID GAS SCRUBBERS

CROSS REFERENCE TO RELATED APPLICATIONS

This application claims the benefit of priority to U.S. Provisional Application No. 61/917,207, filed Dec. 17, 2013, and EP 14153946.0 filed Feb. 2, 2014, the disclosures of which are fully incorporated herein by reference.

BACKGROUND OF THE INVENTION

Field

The invention generally relates to processes for reducing condensation in an acid gas scrubbing tower useful for upgrading a hydrocarbon-containing stream, such as hydrocarbon streams containing C2+ mono-olefins, diolefin, and one or more acidic gases, equipment useful in such processes, and upgraded process streams produced using the same.

Description of Related Art

Olefins can be used to produce many useful products. For example, ethylene and/or propylene can be polymerized to produce polymer, such as polyethylene, polypropylene, ethylene-propylene copolymer, etc. Olefins can be produced by many conventional processes, including: (1) catalytically converting alcohol, such as methanol; (2) pyrolysing a hydrocarbon-containing feed, as in steam cracking; or (3) catalytically cracking a hydrocarbon feed, as in fluidized catalytic cracking, hydrocracking, etc. Besides olefins, effluents from these processes can contain acidic gases, e.g., $H_2S$, $CO_2$, etc. When the feeds to these processes contain sulfur and/or sulfur-containing molecules, such as in the catalytic cracking and/or steam cracking of heavy oil and/or one or more fractions thereof, the acidic gases generally include $H_2S$. The effluent can also contain diolefin molecules, for example, propadiene, cyclopentadiene, isoprene, or butadiene. This is especially true when steam cracking is utilized for producing the olefins.

It is conventional to utilize amine and/or caustic for removing one or more acidic gases from a process stream containing olefins. For example, $CO_2$ and $H_2S$ can be removed from a steam cracker effluent by contacting the effluent with a caustic and/or amine scrubbing solution, e.g., by an acid gas scrubbing process in caustic or amine scrubbing towers.

The amine scrubbing solution absorbs the acid gases like $CO_2$ and $H_2S$ and removes them from the olefins process stream. The scrubbing solution containing the acid gases exits the scrubbing tower and is conducted to an amine regeneration system where the solution is heated to release the acid gases. The scrubbing solution exiting the regeneration system, mostly free of acid gases, is returned to the scrubbing tower.

In a caustic scrubbing tower, the acid gases such as $CO_2$ and $H_2S$ are absorbed and react in the caustic scrubbing solution to form caustic salts and water. The caustic scrubbing solution is recirculated by pumps through the caustic tower. The caustic salts are removed from the circulating scrubbing solution in a spent caustic stream for disposal while a fresh caustic stream is added to maintain an optimal caustic scrubbing solution.

A significant hurdle to operation of acid gas scrubbing process, e.g., caustic or amine scrubbing towers, is buildup of polymerized foulant. Polymerization fouling can cause the acid gas scrubbing system to limit capacity for the broader olefin production process resulting in significant negative financial impact. An improved process is therefore desired which reduces the buildup of polymerized foulant in the acid gas scrubbing system.

SUMMARY OF THE INVENTION

The present invention is directed to a process and apparatus that satisfies this need. It has been observed that polymerization fouling problems in the amine regeneration system are caused, at least in part, by the heat reactive diolefins present in the acid gas being carried into the amine scrubbing solution. Similarly, diolefin polymerization in a caustic scrubber tower may be caused, at least in part, by shearing in the caustic scrubbing system pumps of reactive diolefin molecules carried from the acid gas into the caustic scrubbing solution.

Superheating the acid gas feed reduces condensation of diolefin hydrocarbons in the acid gas scrubbing tower. This reduces the amount of diolefins carried into the acid gas scrubbing solution thereby reducing the amount of diolefin polymerization.

Superheating may be accomplished in a grass roots facility using a conventional heat exchanger. But retrofitting a heat exchanger to an existing facility may not be feasible due to size or timing constraints. The present invention represents an alternative, low cost solution that requires minimal modification to existing facilities. The present invention is also useful when attempting to upgrade existing facilities to process heavier feeds which produce more diolefin.

The invention generally relates to a hydrocarbon process for reducing condensation in a vapor-liquid amine or caustic acid gas scrubber. The process comprises a number of steps. First, a first mixture is provided, the first mixture being superheated and comprising $C_{2+}$ mono-olefin, acid gases, and diolefin molecules. Second, the first mixture is divided into a first stream and a second stream, the first and second streams having substantially the same composition. Third, the first stream is cooled to produce a gas phase and a liquid phase, the gas phase comprising less $C_{6+}$, the liquid phase containing more $C_{6+}$. Fourth, the gas phase is separated to create a third stream. Fifth, the third stream and the second stream are combined to form a second substantially superheated mixture. Sixth, the second mixture is conducted to an acid gas scrubbing tower.

The invention also generally relates to an apparatus for reducing condensation in a vapor-liquid amine or caustic acid gas scrubber. The apparatus comprises: (i) a superheated feed source and a cooling heat exchanger connected in fluid communication by a feed conduit; (ii) a gas-liquid separation drum in fluid communication with the cooling heat exchanger, the gas-liquid separation drum comprising a gas phase section and a liquid phase section; (iii) an acid gas scrubbing tower connected by a gas effluent conduit to the gas phase section of the gas-liquid separation drum; and (iv) a bypass fluid communication line connecting the feed conduit to the gas effluent conduit.

These and other features, aspects, and advantages of the present invention will become better understood with regard to the following description, appended claims, and accompanying drawings.

BRIEF DESCRIPTION OF THE DRAWINGS

FIG. 1 schematically illustrates an apparatus for reducing condensation in a vapor-liquid acid gas scrubber.

DETAILED DESCRIPTION OF THE INVENTION

Definitions

When numerical lower limits and numerical upper limits are listed herein, ranges from any lower limit to any upper limit are contemplated. The term "comprising" is synonymous with the term "including". Likewise whenever a composition, an element or a group of components is preceded with the transitional phrase "comprising", it is understood that we also contemplate the same composition or group of components with transitional phrases "consisting essentially of," "consisting of", "selected from the group of consisting of," "including," or "is" preceding the recitation of the composition, component, or components, and vice versa.

Description

Many common methods for producing unsaturated hydrocarbons, e.g. catalytic cracking, hydrocracking, catalytically converting alcohols to olefins, steam cracking, etc., produce an effluent process stream containing olefins, including $C_{2+}$ mono-olefins. Often, these streams also contain acidic heteroatom-containing molecules such as one or more of $CO_2$, $H_2S$ or other acidic gases, and diolefins, such as propadiene, cyclopentadiene, isoprene, or butadiene.

It has been observed that polyunsaturated molecules, e.g., diolefins, are produced in a reducing atmosphere, e.g., when produced by a steam cracking process having a significant molecular hydrogen yield. Diolefin concentration is relatively higher when feeds such as heavy oil and oil fractions (such as gas oils) are utilized because these feeds result in less molecular hydrogen in the process stream.

When process streams contain lower amounts of $H_2S$, e.g., $\geq 10$ ppmw and $\leq 1.5 \times 10^3$ ppmw, based on the weight of the process stream, it is conventional to remove at least a portion of the $CO_2$ or $H_2S$ from process streams containing olefin hydrocarbons by contacting the process stream with a base, e.g., with an aqueous mixture comprising one or more bases such as sodium hydroxide (NaOH), which is a caustic scrubbing solution. At higher $H_2S$ concentrations, e.g., $>1.5 \times 10^3$ ppmw, based on the weight of the process stream, it is conventional to remove at least a portion of the $CO_2$ or $H_2S$ from process streams containing olefin hydrocarbon by contacting the process stream with amine, e.g., with an aqueous mixture comprising one or more amines, which is an amine scrubbing solution.

Contact with this scrubbing solution may be accomplished after the process stream has been compressed by a multi-stage compression system. Contact with this scrubbing solution may also be accomplished as an intermediate step between stages of a multi-stage compression system. The energy imparted to the process stream by the compressor leaves the process stream superheated. The superheated process stream is sent through an inter-stage cooler and a vapor-liquid separation drum to separate a portion of the heavier hydrocarbons contained in the stream. The vapor phase effluent, now at its dew point, leaves the separation drum and is fed to a countercurrent vapor-liquid contact vessel often called "absorber," "scrubber," or "tower," e.g., caustic scrubber or amine scrubber.

Caustic scrubbers function by absorption and reaction of the acid gas components, e.g., $CO_2$ or $H_2S$, with aqueous [Na$^+$] and [OH$^-$] ions to produce sodium sulfide (Na$_2$S), sodium hydrosulfide (NaHS), sodium carbonate (Na$_2$CO$_3$), and sodium bicarbonate (NaHCO$_3$) which are absorbed into the caustic solution and, thus removed from the process gas stream. To prevent buildup of the concentration of these components in the caustic scrubbing solution, a quantity of spent caustic is replaced by an amount of fresh caustic. Additionally, the caustic scrubbing solution is circulated through the scrubber to provide proper vapor liquid contact. The spent caustic is conditioned by further processing steps in a spent caustic treatment unit to condition it for an environmentally sound disposal.

Amine scrubbers function similarly by absorption and reaction of the acid gas components with a "lean" aqueous amine scrubbing solution. After contacting the process stream (and absorbing at least a portion of one or more of the process stream's acidic gases) the lean aqueous amine mixture becomes a "rich" aqueous amine mixture. Such rich aqueous amine mixtures generally have acidic gas content (molar basis) in the range of 40% to 50% (mole of acid gas per mole of amine) The rich amine mixture contains one or more of [HS—] ions, carbamate ions, or bicarbonate ions removed from the process stream. Absorption of $H_2S$ occurs by solubility and reaction with the free amine and the protonated amine to yield soluble hydrosulfide species. The removal of $CO_2$ involves carbamate and bicarbonate pathways.

During the contacting of the process stream with the aqueous amine scrubbing solution in the amine scrubber, the pressure is relatively high and temperature is relatively low, resulting in $H_2S$ and $CO_2$ absorption from the process stream into the lean aqueous amine mixture to produce the rich aqueous amine mixture. The rich aqueous amine mixture can be regenerated by exposing it to a higher temperature and lower pressure than that utilized during $CO_2$ and $H_2S$ absorption, in order to evolve those molecules and produce a regenerated aqueous amine mixture. The regenerated aqueous amine mixture can be utilized (e.g., by re-cycling) as the lean aqueous amine mixture or a component thereof It is believed that diolefins are carried into the amine or caustic scrubbing solution by at least the mechanism where the scrubbing solution condenses some heavier hydrocarbons which are saturated with diolefins. Polymerization of the diolefin then occurs in the amine or caustic scrubbing system.

In the caustic scrubber the highly reactive diolefins undergo addition type polymerization to various degrees, even to the point of reaching a molecular weight which renders certain polymer species insoluble in the caustic scrubbing solution such that they precipitate out of solution. It is believed the polymerization is furthered, at least partly, by the shearing forces of caustic scrubbing solution circulation pumps. The polymers are recirculated through the scrubber and coat, foul, and plug the internals of the caustic scrubber, which at times necessitates shutdown of the scrubber.

For the amine scrubber, the polymerization buildup may occur after exposure to hot temperature in the amine regeneration equipment. The diolefin polymers adhere to the scrubbing and regeneration equipment (and the interconnecting piping) utilized for the $CO_2$ and/or $H_2S$ removal, resulting in a loss of removal efficiency of $CO_2$ and $H_2S$ from the process stream (during scrubbing with the lean aqueous amine mixture) and from the rich aqueous amine mixture during regeneration. Removing the deposited polymer, generally with the scrubber and/or the regenerator off-line, is time consuming and expensive.

The buildup of polymer can be mitigated by preventing some of the diolefin molecules from being carried into the caustic or amine scrubbing solution. Superheating the acid gas process stream above the dew point of the acid gas stream prior to contact with the scrubbing solution reduces the amount of diolefins that condense in the acid gas scrubber. Fewer condensed diolefin molecules reduces the amount of the same that are carried into the scrubbing solution thereby reducing the amount of diolefin polymerization.

Superheating the acid gas stream to reduce condensation in an acid gas scrubbing tower may be accomplished using an apparatus schematically represented in FIG. 1. The apparatus 10 comprises a superheated feed source 100, e.g., a discharge from a multi-stage compressor, and a cooling heat exchanger 110 connected in fluid communication by feed conduit 101. The cooling heat exchanger 110 and gas-liquid separation drum 120 are connected via fluid communication line 111. Liquid in a liquid phase section 126 of the gas-liquid separation drum 120 may be conducted away via fluid communication line 122. A gas effluent conduit 121 connects gas phase section 125 of the gas-liquid separation drum 120 to the acid gas scrubbing tower 130. Bypass fluid communication line 102 connects feed conduit 101 with gas effluent conduit 121. Bypass fluid communication line 102 transports a portion of superheated feed fluid around cooling heat exchanger 110 and gas-liquid separation drum 120. Fluid communication line 103 represents the section of feed conduit 101 that is downstream of the bypass fluid communication line 102 connection. Fluid communication line 131 represents the section of gas effluent conduit 121 that is downstream of the bypass fluid communication line 102 connection. Process gas may be conducted away from scrubbing tower 130 via communication line 132. Scrubbing solution may be conducted to the scrubbing tower 130 via fluid communication line 133 and conducted away via line 134.

Conventional cooling heat exchangers can be utilized in the apparatus, e.g., counter-current or co-current shell and tube or plate and fin heat exchangers, though the invention is not limited thereto.

Conventional gas-liquid separator can be utilized in the apparatus, though the invention is not limited thereto. Generally, when using a gas-liquid separation device, the composition of the gas phase leaving the device is substantially the same as the composition of the gas phase entering the device, and likewise the composition of the liquid phase leaving the gas-liquid separator is substantially the same as the composition of the liquid phase entering the separator, e.g., the separation in the gas-liquid separator can be a physical separation of the two phases entering the drum.

Conventional amine or caustic scrubbing towers can be utilized in the apparatus. For example, counter-current vapor-liquid amine absorber and regenerator systems or multi-section caustic towers with an incorporated water wash section can be used, though the invention is not limited thereto.

One advantage of the invention is the pre-existing cooling heat exchanger, gas-liquid separator, and acid gas scrubbing tower are typically of adequate size, material, and configuration when retro-fitting the apparatus into existing facilities. For new facilities, conventional design methods, e.g., computer simulation and industrial design standards, may be used to design the heat exchanger, gas-liquid separator, and acid gas scrubbing tower.

The bypass fluid communication line sizing may be determined via conventional design methods, e.g., computer simulation and industrial design standards, so that sufficient flow is provided to superheat the combined feed to the acid gas scrubbing tower. An advantage of the present invention is installing a bypass fluid communication line may be low cost and short duration implementation compared to installing a conventional heat exchanger for superheating the acid gas scrubber feed.

The bypass fluid communication line may include a flow control device. For example, a restriction orifice, equal-percentage, butterfly, or other flow control device may be utilized.

The bypass fluid communication line may also include a gas-liquid separator as described above. The gas-liquid separator in the bypass fluid communication line may be sized differently, e.g., smaller or larger, than the gas-liquid separator downstream of the cooling heat exchanger, depending on the amount of liquid in the uncooled acid gas stream and the amount of flow through the bypass fluid communication line. The two gas-liquid separators may also be of different or the same design.

The invention apparatus may include a temperature measuring device located to provide the temperature of the fluid downstream of the bypass fluid communication line connection to the gas effluent conduit from the gas-liquid separation drum. Referring to the schematic representation in FIG. 1, the temperature measuring device can be located to provide the temperature of the fluid in fluid communication line 131. Any conventional temperature measuring device can be utilized for the apparatus, e.g., thermowell and thermocouple, but the invention is not limited thereto.

A process for superheating the acid gas process stream to reduce condensation in an acid gas scrubbing tower may be accomplished by providing a first mixture comprising $C_{2+}$ mono-olefin, acid gas, e.g. $H_2S$, $CO_2$, or other acidic gases, and diolefin molecules. The first mixture may be a process stream comprising, e.g., diolefins, ≥10.0 wt. % of $C_{2+}$ olefins; ≥1.0 wt. % of $C_{6+}$ aromatics; ≥0.1 wt. % total RSH, where R is one or more of hydrogen or $C_{1+}$ alkyl or isoalkyl; and ≥0.1 wt. % $CO_2$, the weight percent being based on the weight of the process stream. For example, the first mixture may comprise diolefin, 15.0 wt. % to 30.0 wt. % $C_{2+}$ olefins; 1.0 wt. % to 30.0 wt. % $C_{6+}$ aromatics; ≥0.1 wt. % total RSH, where R is one or more of hydrogen or $C_1$ to $C_4$ alkyl and/or isoalkyl; and 0.1 wt. % to 5.0 wt. % $CO_2$. Typically, the first mixture comprises ≥0.01 wt. % diolefin, e.g., ≥0.1 wt. % diolefin, based on the weight of the first mixture. The first mixture may comprise ≥1.0 ppmw mercaptans, e.g., ≥10.0 ppmw, ≥10.0 ppmw mercaptans, based on the weight of the first mixture. The first mixture may also comprise ≥10 ppmw $H_2S$, e.g., ≥100 ppmw, ≥1.5×10³ ppmw $H_2S$, based on the weight of the first mixture.

In a more specific example, the first mixture may comprise (i) ≥10.0 wt. % $C_{2+}$ olefins, (ii) ≥1.0 wt. % aromatics, (iii) ≥10.0 ppmw mercaptans, and (iv) ≥10 ppmw $H_2S$, the weight percent and ppmw being based on the weight of the first mixture. Additionally, the first mixture may comprise higher amounts of $H_2S$. When the first mixture is produced by steam cracking a heavy oil fraction, the first mixture may comprise (i) ≥10.0 wt. % $C_{2+}$ olefins, (ii) ≥1.0 wt. % aromatics, (iii) ≥100.0 ppmw mercaptans, and (iv) ≥1.5×10³ ppmw $H_2S$, the weight percent and ppmw being based on the weight of the first mixture.

The first mixture should be superheated. Preferably, the first mixture is superheated, e.g., ≥5° C., ≥10° C., ≥15° C., ≥20° C., ≥25° C., ≥30° C., ≥35° C., ≥40° C., or ≥50° C., above the dew point of the first mixture.

The first mixture is divided to into a first stream and a second stream where the two streams have substantially the same composition. The second stream mass flow may be a percent, e.g., ≥5%, ≥10%, ≥15%, ≥20%, ≥25%, ≥50%, or ≥75%, of the first mixture mass flow.

The first stream is cooled so that a portion of the first stream components condense. Thus, a liquid and a gas phase may form from the first stream components. The liquid phase contains relatively higher dew point components, e.g., heavier hydrocarbons such as aromatics, while the gas phase contains relatively lower dew point components, e.g., lighter hydrocarbons such as propane, such that the liquid phase contains more $C_{6+}$ hydrocarbons and the gas phase contains less $C_{6+}$ hydrocarbons. The gas phase and liquid phase may be at vapor-liquid equilibrium so that the gas phase is at its dew point temperature. In other words, if the gas phase were further cooled, more components would condense. The gas phase may be separated away from the liquid phase to form a third stream containing acid gas process stream at its dew point temperature.

The second stream containing superheated acid gas (diverted from the superheated first mixture) is combined with the third stream to produce a substantially superheated acid gas second mixture. In other words, the temperature of the second mixture is above the dew point for substantially all the components of the second mixture. The second mixture is superheated (e.g., ≥2° C., ≥3° C., ≥4° C., ≥5° C., ≥6° C., ≥8° C., ≥10° C., ≥12° C., ≥15° C., ≥20° C., or ≥25° C.) above the dew point of the second mixture. The superheated second mixture is then conducted to an acid gas scrubbing tower, e.g. a caustic or amine scrubbing tower.

Referring to apparatus schematic representation in FIG. 1, the process for superheating an acid gas process stream to reduce condensation in an acid gas scrubbing tower comprises providing a first mixture comprising superheated $C_{2+}$ mono-olefin, acid gas, and diolefin molecules as superheated feed source 100. The first mixture is divided into a first stream in fluid communication line 103 and a second stream of substantially the same composition in bypass fluid communication line 102. The first stream is cooled in a cooling heat exchanger 110 to produce a gas phase containing less $C_{6+}$ and a liquid phase containing more $C_{6+}$. The gas phase and liquid phase is conducted via fluid communication line 111 to a gas-liquid separator 120 where the gas phase is separated from the liquid phase to form a third stream. The third stream is conducted via gas effluent conduit 121 to a point where the third stream is combined with the second stream conducted via bypass fluid communication line 102. The second and third streams are combined to form a superheated second mixture comprising $C_{2+}$ mono-olefin (less some $C_{6+}$ hydrocarbons), acid gas, and diolefin molecules. The second mixture is conducted via fluid communication line 131 to an acid gas scrubber 130, e.g., an amine or caustic scrubbing tower.

EXAMPLES

An illustrative example was prepared using computer simulation based on observed conditions in an operating olefins steam cracking process. The results of the simulation are presented in Table 1 and described below.

TABLE 1

| | Base Case (No Bypass) | With Bypass |
|---|---|---|
| First Mixture Temperature (° C.) | 78 | 78 |
| Percent Bypass (%) | 0 | 24 |
| Third Stream Temperature (° C.) | 39 | 36 |
| Content of Fluid Communication Line 131 Temperature (° C.) | 39 | 47 |
| Content of Fluid Communication Line 131 | 39 | 41 |

TABLE 1-continued

| | Base Case (No Bypass) | With Bypass |
|---|---|---|
| Dew Point (° C.) | | |
| Content of Fluid Communication Line 131 Degrees of Superheat (° C.) | 0 | 6 |

Referring to FIG. 1, a first mixture of superheated $C_{2+}$+mono-olefin, acid gas, and diolefin molecules at 78° C. was provided as superheated feed source 100. The first mixture was divided into a first stream in fluid communication line 103 and a second stream of substantially the same composition in bypass fluid communication line 102. The mass flow rate of the second stream was adjusted to target a percent of bypass flow diverted from the first mixture, the percent based on the first mixture mass flow rate. A base case of 0% bypass (no bypass flow in the second stream) was simulated to compare against an example simulation case of 24% bypass (24% of the first mixture flow was diverted to the second stream).

In both cases, the first stream was cooled in a cooling heat exchanger 110 to produce a gas phase containing less $C_{6+}$ and a liquid phase containing more $C_{6+}$. The gas phase and liquid phase was conducted via fluid communication line 111 to a gas-liquid separator 120 where the gas phase was separated from the liquid phase to form a third stream conducted via gas effluent conduit 121. The temperature of the third stream is summarized in Table 1. It was noted that the third stream temperature decreased as percent bypass increased due to decreased flow through the cooling heat exchanger.

In the base case, the third stream was conducted directly to fluid communication line 131 without being combined with any bypass. The temperature, dew point, and degrees of superheat are indicated in Table 1.

In the 24% bypass case, the third stream was conducted via gas effluent conduit 121 to a point where the third stream was combined with the second stream conducted via bypass fluid communication line 102. The second and third streams were combined to form a superheated second mixture comprising $C_{2+}$ mono-olefin (less some $C_{6+}$ hydrocarbons), acid gas, and diolefin molecules. The temperature, dew point, and degrees of superheat of the second mixture in fluid communication line 131 are indicated in Table 1. It was noted that the 24% bypass case had 6° C. of superheat while the 0% bypass base case showed no superheat.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

What is claimed is:
1. A hydrocarbon process for reducing condensation in an acid gas scrubber, comprising:

(a) providing a first mixture, the first mixture (i) being superheated and (ii) comprising acid gases and $C_{2+}$ hydrocarbons including mono-olefins and di-olefins;

(b) dividing the superheated first mixture into a first stream and a second stream;

(c) cooling the first stream to produce a gas phase and a liquid phase, the gas phase comprising less $C_{6+}$ hydrocarbons, the liquid phase containing more $C_{6+}$ hydrocarbons;

(d) separating the gas phase from the liquid phase to create a third stream comprising the gas phase;

(e) combining the third stream and the second stream to form a second superheated mixture to reduce condensation; and (f) conducting the second mixture to an acid gas scrubber.

2. The process of claim 1, wherein the first mixture comprises (i) $\geq 10.0$ wt. % olefins, (ii) $\geq 1.0$ wt. % aromatics, (iii) $\geq 10.0$ ppmw mercaptans, and (iv) $\geq 10$ ppmw $H_2S$, the weight percent and ppmw based on the weight of the first mixture.

3. The process of claim 1, wherein the first mixture comprises (i) $\geq 10.0$ wt. % olefins, (ii) $\geq 1.0$ wt. % aromatics, (iii) $\geq 100.0$ ppmw mercaptans, and (iv) $\geq 1.5 \times 10^3$ ppmw $H_2S$, the weight percent and ppmw based on the weight of the first mixture.

4. The process of claim 1, wherein the temperature of the second mixture is $\geq 2°$ C. above the dew point of the second mixture.

5. The process of claim 1, wherein the second stream mass flow rate is $\geq 5\%$ of the first mixture mass flow rate.

* * * * *